US012472310B1

(12) United States Patent
Hendon

(10) Patent No.: US 12,472,310 B1
(45) Date of Patent: Nov. 18, 2025

(54) NEEDLE CARTRIDGE ASSEMBLY AND METHODS FOR SKIN TREATMENT USING SAME

(71) Applicant: Redon LLC, Athens, GA (US)

(72) Inventor: Ronald Trevor Hendon, Athens, GA (US)

(73) Assignee: Redon LLC, Athens, GA (US)

( * ) Notice: Subject to any disclaimer, the term of this patent is extended or adjusted under 35 U.S.C. 154(b) by 110 days.

(21) Appl. No.: 18/599,009

(22) Filed: Mar. 7, 2024

Related U.S. Application Data

(60) Provisional application No. 63/451,828, filed on Mar. 13, 2023.

(51) Int. Cl.

| | |
|---|---|
| ***A61B 17/00*** | (2006.01) |
| ***A61M 5/24*** | (2006.01) |
| ***A61M 5/32*** | (2006.01) |
| ***A61M 37/00*** | (2006.01) |

(52) U.S. Cl.
CPC ........... *A61M 5/3221* (2013.01); *A61B 17/00* (2013.01); *A61M 5/2425* (2013.01); *A61B 2017/00769* (2013.01)

(58) Field of Classification Search
CPC .......... A61M 37/0076; A61M 37/0084; A61M 5/24; A61B 2017/00769
See application file for complete search history.

(56) References Cited

U.S. PATENT DOCUMENTS

2013/0197560 A1* 8/2013 Cheng ............... A61M 37/0076 606/186
2017/0065807 A1* 3/2017 Niven .................... A61B 17/00

* cited by examiner

*Primary Examiner* — Tuan V Nguyen
(74) *Attorney, Agent, or Firm* — TILLMAN WRIGHT, PLLC; David R. Higgins; James D. Wright

(57) ABSTRACT

A needle cartridge assembly for use with a pen for treatment of skin discoloration or scarring includes each of a housing and a needle affixed to a plunger. The housing has an interior cavity, an end with an opening, and a bulbous portion at or near a midsection that is adapted to retain a removal solution. The plunger is arranged at least partially within the housing, and the needle includes a plurality of pins extending from an end thereof. The needle is adapted to be displaceable longitudinally through the interior cavity to maneuver the plurality of pins through the opening. The plurality of pins is adapted to flare outward at least upon passing through the opening.

20 Claims, 7 Drawing Sheets

150

NEEDLE CARTRIDGE ASSEMBLY AND METHODS FOR SKIN TREATMENT USING SAME

CROSS-REFERENCE TO RELATED APPLICATIONS

The present application is a U.S. nonprovisional patent application of, and claims priority under 35 U.S.C. § 119 (e) to, U.S. provisional patent application Ser. No. 63/451,828, filed Mar. 13, 2023, which '828 application is incorporated by reference herein in its entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to needle cartridge assemblies for tattoo pens, and, in particular, to needle cartridge assemblies for use in connection with a tattoo removal and/or scar reduction process.

Background

Pens and applicators for the creation of a tattoo in the skin are well known. Pens are commonly designed to be hand-held so that the pen can be held in a manner similar to that of a conventional writing instrument. One end of the pen is connectable to a power supply, and the other end employs a removable needle cartridge assembly for use in piercing and embedding ink into the skin.

FIG. 1A is a top plan view of a conventional needle cartridge assembly 10 for use with a tattoo pen, and FIG. 1B is a side plan view of the conventional needle cartridge assembly 10 of FIG. 1A. The needle cartridge assembly 10 includes a housing 14 and a tattoo needle (not visible in FIGS. 1A and 1B) affixed to a plunger 16. The housing 14 is securable to a tattoo pen and may include surface features 12 to facilitate such securement. As shown in FIGS. 1A and 1B, a rear portion of the housing 14 is designed to be seated within the pen such that a ledge 20 of the housing rests against a distal end of the pen. A front portion of the housing 14 is tapered toward a tip 18, which includes an opening 22 through which the needle can pass. With reference to FIG. 1B in particular, the housing 14 also includes one or more side openings 28, commonly referred to as "washouts," to allow excess ink from within the housing 14 to drain. The plunger 16, which is arranged largely within the internal cavity of the housing 14, is visible through the washout 28.

FIG. 1C is a top plan view of the conventional needle cartridge assembly 10 of FIG. 1A, shown with the needle 30 protruding from the tip 18 of the housing 14, and FIG. 1D is a side plan view of the conventional needle cartridge assembly 10 of FIG. 1C. The plunger 16 is shown as a cylindrical rod that extends along the interior cavity of the housing 14 and through an endcap 24 seated at a rear of the housing 14. At a forward end, the plunger 16 includes a tattoo needle 30 that is arranged within the cylindrical profile of the plunger 16. As shown in FIGS. 1C and 1D, the plunger 16 is displaceable along its longitudinal axis by a force, designated by an arrow in FIGS. 1C and 1D, which acts upon the rear end thereof. When applied, the force shifts the plunger 16 forward, against a bias, by a distance that is sufficient for the needle 30 to protrude from the opening 22 at the tip 18 of the housing 14. When the force is withdrawn, the plunger 16 is biased to return to a resting state, with the needle 30 retracting into the internal cavity of the housing 14.

FIG. 1E is a close-up top plan view of the conventional needle cartridge assembly 10 of FIG. 1C, illustrating an arrangement of individual pins 32 of the needle 30, and FIG. 1F is a front end plan view of the conventional needle cartridge assembly 10 of FIG. 1C. The needle 30 includes a plurality of solid pins each of which includes a tapered distal end that arrives at a point sharp enough to pierce skin. The arrangement, or grouping, of pins 32 can vary from needle to needle. As shown in FIG. 1F, the illustrated needle 30 includes thirteen individual pins 32 in a circular ring-like arrangement, which is commonly referred to as a "13 round shader" arrangement. The "13 round shader" designation is also sometimes used in reference to needles with other arrangements that feature thirteen individual pins. For example, FIG. 1G is a front end plan view of another conventional needle cartridge assembly 11 shown with a needle 31 protruding from a tip 18 of a housing 14 and having an alternative arrangement of individual pins 33 of the needle 31. As shown in FIG. 1G, the pins 33 of the needle 31 are clustered together. In such cases, the pins 33 may still be characterized as having a generally circular arrangement (or, in some cases, a star-shaped arrangement), but without a ring-like appearance (i.e., the circle or star shape includes pins situated interiorly of the shape).

Due to the need for precision in applying ink to the skin, an acceptable working diameter for a round shader arrangement is generally about 1.3 mm to 1.4 mm with individual pin diameter no larger than 0.35 mm. In each of the variations shown in FIGS. 1F and 1G, the pins 32,33 of the needle 30,31 are in parallel alignment with one another and with the cylindrical axis of the plunger 16. In this manner, the pins 32,33 remain within the cylindrical profile of the plunger 16 even when protruding from the housing 14.

The conventional needle cartridge assembly 10,11 of FIGS. 1A-1G is adapted for use with a tattoo pen to introduce ink to the skin in connection with a tattooing process. When the needle cartridge assembly 10,11 is seated onto a tattoo pen, the rear end of the plunger 16 is positioned against an actuatable structure of the pen. The tattoo pen, which is commonly powered via a DC power source, can be used to actuate the structure to apply a temporary force to the rear end of the plunger 16, thereby deploying the needle as the force is applied and then allowing the needle 30,31 to retract as the force is removed. In operation, the tattoo pen actuates the structure at rapid intervals to facilitate deployment and retraction of the needle 30,31 with each actuation-a state that can be characterized as an "active" state. The pace of needle deployment and retraction during the active state is commonly at a level that is sufficient to cause the pen to vibrate.

In connection with a tattooing process, the pen is dipped into a tattoo ink of a desired pigment. Ink is drawn into the needle 30,31, generally between and among individual pins 32,33 thereof, by capillary action. Once ink is drawn up by a sufficient margin, ink begins to fill the internal cavity of the housing 14. During the tattooing process, too much ink can result in oversaturation of ink in the skin and the inability to apply the ink to the skin with precision. To help maintain an appropriate volume of ink within the housing 14, excess ink at the internal cavity can be drained via the washouts 28.

With ink retained in the needle 30,31 or the internal cavity of the housing 14, the pen is activated, and the tip 18 of the housing 14 is placed near or against the area to be tattooed. During deployment of the needle 30,31, individual pins 32,33 pierce the skin and allow ink to be deposited, by gravity, to the skin. Due to the small diameter of the pin arrangement and the limited capacity for ink retention within the housing 14 and needle 30,31, ink can be applied with precision and accuracy, which enhances the ability of the tattoo artist to employ artistic skill and technique in the process.

Though the conventional needle cartridge assembly 10,11 of FIGS. 1A-1G is well suited to embed ink in the skin in connection with a tattooing process, it is not as suitable for a process of removing tattoos or reducing scars. Despite tattoos being designed for permanence, a growing market exists for tattoo removal. Current removal processes employ conventional needle cartridge assemblies in accordance with that which is set forth in connection with FIGS. 1A-1G or similar devices. However, tattoo removal utilizes a specialized removal solution in lieu of ink in the needle cartridge assembly. The removal process can be time-sensitive, and it is often a challenge to deploy the removal solution in an effective manner using an instrument designed for precision tattooing. This challenge is compounded by the fact that, in order to help optimize effectiveness, the removal solution should be applied not just to skin with embedded pigment, but also to the surrounding skin. Use of a higher volume of solution requires a higher storage capacity than conventional needle cartridge assemblies are intended to hold. The above-described challenges that are common to a tattoo removal process apply similarly to the scar reduction process. For example, scar reduction generally requires higher solution volume as well as treatment across a wider skin area than simply where the scar is located.

Another known process that has been utilized in connection with tattoo removal or reduction is microneedling, which is also known as collagen induction therapy. With microneedling, a grouping of sterile needles is used to create small holes in the outer layer of skin to prompt the skin to heal itself. Though commonly used to treat skin conditions such as scarring or acne, microneedling has also been used to encourage skin rejuvenation in areas where skin includes embedded pigment from a tattooing process. In conventional microneedling processes, individual needles are more spaced apart than is typical in a conventional needle cartridge assembly 10,11, as in FIGS. 1A-1G. However, microneedling devices are generally not designed to be used in connection with retention or administration of liquids.

Accordingly, a need exists for a needle cartridge assembly that is effective for retaining and administering a liquid solution to the skin for tattoo removal and/or scar reduction. This and/or other needs are addressed by one or more aspects of the present invention.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

The present invention includes many aspects and features. Moreover, while many aspects and features relate to, and are described in, the context of needle cartridge assemblies for tattoo pens, the present invention is not limited to use only in needle cartridge assemblies for tattoo pens, as will become apparent from the following summaries and detailed descriptions of aspects, features, and one or more embodiments of the present invention.

Broadly defined, the present invention according to one aspect relates to a needle cartridge assembly for use in connection with a pen for tattoo removal and/or scar reduction. The needle cartridge assembly includes a housing and a needle affixed to a plunger. The housing has an interior cavity, an end with an opening, and a bulbous portion at a midsection that is adapted to retain a liquid removal solution. The plunger is arranged at least partially within the housing, and the needle includes a plurality of pins extending therefrom. The needle is adapted to be displaceable to maneuver the plurality of pins through the opening, and the plurality of pins is adapted to flare outward as the needle is displaced.

In a feature of this aspect, the plurality of pins has a shape in profile. In another feature of this aspect, the plurality of pins retains the shape as the needle is displaced. In another feature of this aspect, a width of the shape gradually increases as the needle is displaced.

In another feature of this aspect, the plurality of pins includes thirteen pins. In another feature of this aspect, the plurality of pins has a round shader arrangement.

In another feature of this aspect, the needle is also adapted to be retractable to withdraw the plurality of pins through the opening and into the interior cavity. In another feature of this aspect, the plurality of pins is adapted to retract inwardly toward one another as the needle is retracted into the interior cavity.

In another feature of this aspect, the bulbous portion has a width exceeding that of any other portion of the housing.

In another feature of this aspect, the housing is made from a clear or translucent material.

In another feature of this aspect, each of the plurality of pins is made from a stainless-steel material.

In another feature of this aspect, the needle cartridge assembly is used in a method of removing a tattoo. In another feature of this aspect, the needle cartridge assembly is used in a method of reducing a scar.

Broadly defined, the present invention according to another aspect relates to a needle cartridge assembly substantially as shown and described.

Broadly defined, the present invention according to another aspect relates to a needle cartridge assembly, for use in connection with a pen for tattoo and/or scar reduction substantially as shown and described.

Broadly defined, the present invention according to another aspect relates to a pen and needle cartridge assembly for tattoo removal and/or scar reduction substantially as shown and described.

Broadly defined, the present invention according to another aspect relates to a method of treating the skin with a liquid removal solution. The method includes: attaching a needle cartridge assembly to a tattoo pen, the needle cartridge assembly including a housing, having an interior cavity and an end with an opening, and a needle arranged at least partially within the housing that includes a plurality of pins; and actuating the needle, via the tattoo pen, to deploy the plurality of pins through the opening, whereupon the plurality of pins flares outward as the needle is deployed.

In a feature of this aspect, a bulbous portion at a midsection is adapted to retain the liquid removal solution.

In another feature of this aspect, upon actuation of the needle, the pins collect the liquid removal solution.

In another feature of this aspect, upon actuation of the needle, the pins pierce skin of a treatment area to deposit the liquid removal solution at a treatment layer of the skin. In another feature of this aspect, pressure is distributed evenly across the pins. In another feature of this aspect, the treatment area includes a tattoo to be removed. In another feature of this aspect, the treatment area includes a scar to be reduced.

In another feature of this aspect, the plurality of pins has a round shader arrangement.

Broadly defined, the present invention according to another aspect relates to a method for tattoo removal substantially as shown and described.

Broadly defined, the present invention according to another aspect relates to a method for scar reduction substantially as shown and described.

Broadly defined, the present invention according to another aspect relates to a needle cartridge assembly for use with a pen for treatment of skin discoloration or scarring. The needle cartridge assembly includes a housing and a needle affixed to a plunger. The housing has an interior cavity, an end with an opening, and a bulbous portion at or near a midsection that is adapted to retain a removal solution. The plunger is arranged at least partially within the housing, and the needle includes a plurality of pins extending from an end thereof. The needle is adapted to be displaceable longitudinally through the interior cavity to maneuver the plurality of pins through the opening. The plurality of pins is adapted to flare outward at least upon passing through the opening.

In a feature of this aspect, the plurality of pins is adapted to flare outward gradually as the needle is displaced.

In another feature of this aspect, the plurality of pins has a shape in profile. In another feature of this aspect, the plurality of pins retains the shape as the plurality of pins flares outward. In another feature of this aspect, a perimeter of the shape after needle displacement through the opening is greater than that of the shape prior to needle displacement through the opening.

In another feature of this aspect, the plurality of pins includes thirteen pins.

In another feature of this aspect, the plurality of pins has a round shader arrangement.

In another feature of this aspect, the needle is adapted to be retractable to withdraw the plurality of pins through the opening and into the interior cavity. In another feature of this aspect, the plurality of pins is adapted to retract inward at least upon passing through the opening into the interior cavity. In another feature of this aspect, the plurality of pins is adapted to retract inward gradually as the needle is retracted into the interior cavity.

In another feature of this aspect, a widest section of the bulbous portion has a width exceeding that of any other portion of the housing. In another feature of this aspect, the bulbous portion includes one or more curved walls.

In another feature of this aspect, each of the plurality of pins is made from a carbon steel material. In another feature of this aspect, one or more of the plurality of pins includes a porous surface along at least a portion of a length thereof.

In another feature of this aspect, each of the plurality of pins is made from a stainless-steel material.

Broadly defined, the present invention according to another aspect relates to a method of treating skin discoloration or scarring. The method includes: attaching a needle cartridge assembly to a pen, the needle cartridge assembly including a housing, having an interior cavity and an end with an opening, and a needle affixed to a plunger that is arranged at least partially within the housing, wherein the needle includes a plurality of pins extending from an end thereof, and wherein the needle is longitudinally displaceable through the interior cavity to maneuver the plurality of pins through the opening; loading the plurality of pins with a removal solution contained at a bulbous portion at or near a midsection of the housing; actuating the needle, via a force applied by the pen against the plunger, to deploy the plurality of pins through the opening, whereupon the plurality of pins flares outward at least upon passing through the opening; and piercing skin of a treatment area via the plurality of pins, thereby depositing at least some of the loaded removal solution at a layer for treatment of skin discoloration or scarring.

In a feature of this aspect, a piercing pressure is distributed evenly across the pins.

In another feature of this aspect, the plurality of pins has a shape in profile that is retained as the plurality of pins flares outward.

In another feature of this aspect, the plurality of pins flares outward gradually as the needle is actuated.

In another feature of this aspect, the plurality of pins has a round shader arrangement.

Further areas of applicability of the present invention will become apparent from the detailed description provided hereinafter. It should be understood that the detailed description and specific examples, while indicating preferred embodiment(s) of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1A:
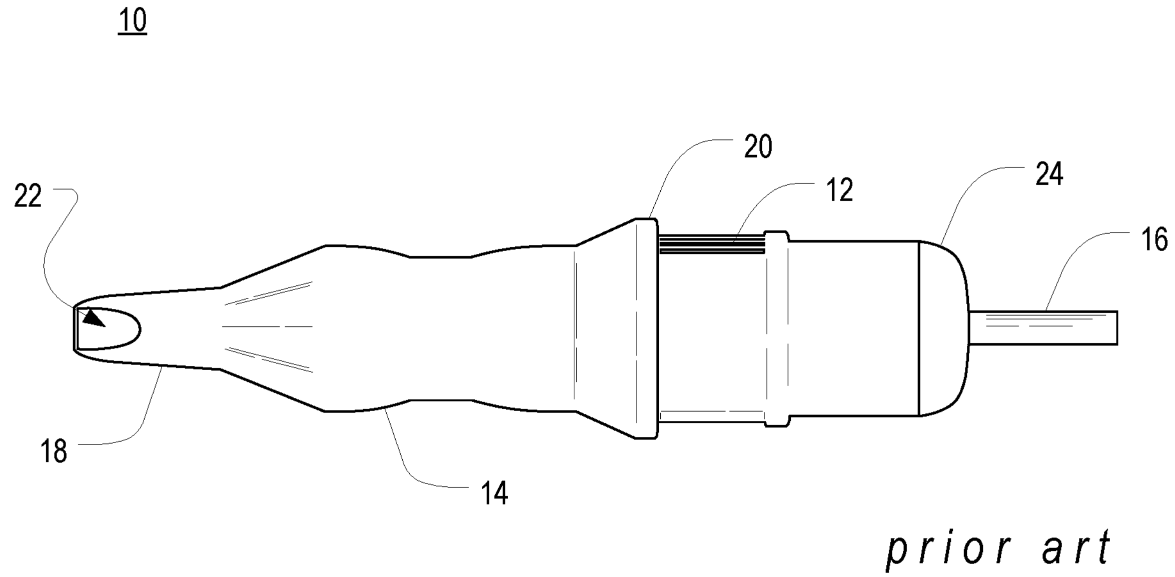
FIG. 1A is a top plan view of a conventional needle cartridge assembly for use with a tattoo pen.
Figure 1B:
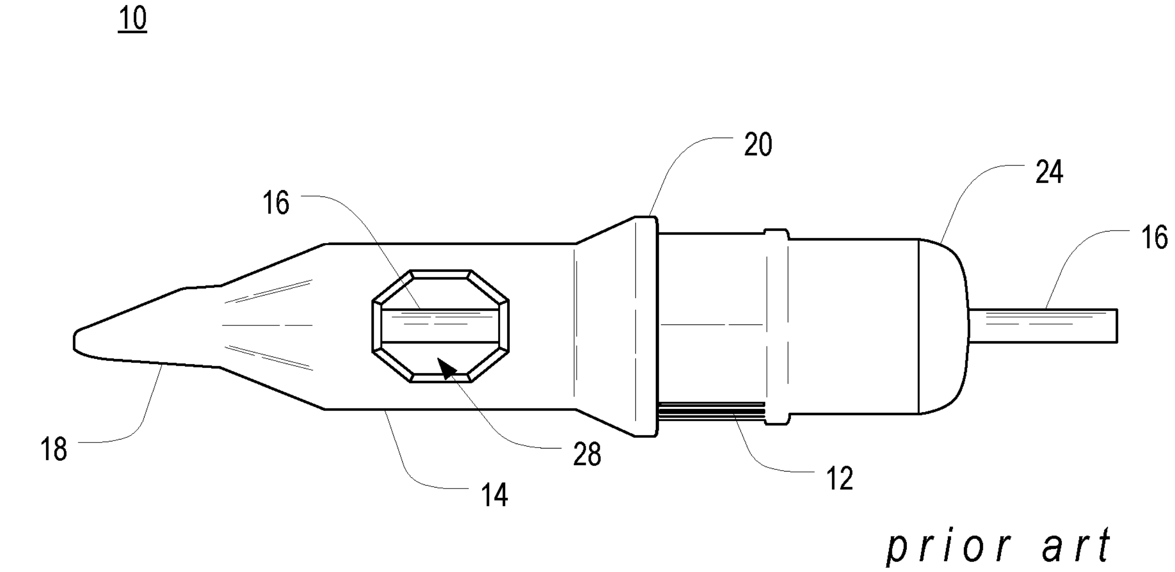
FIG. 1B is a side plan view of the conventional needle cartridge assembly of FIG. 1A.
Figure 1C:
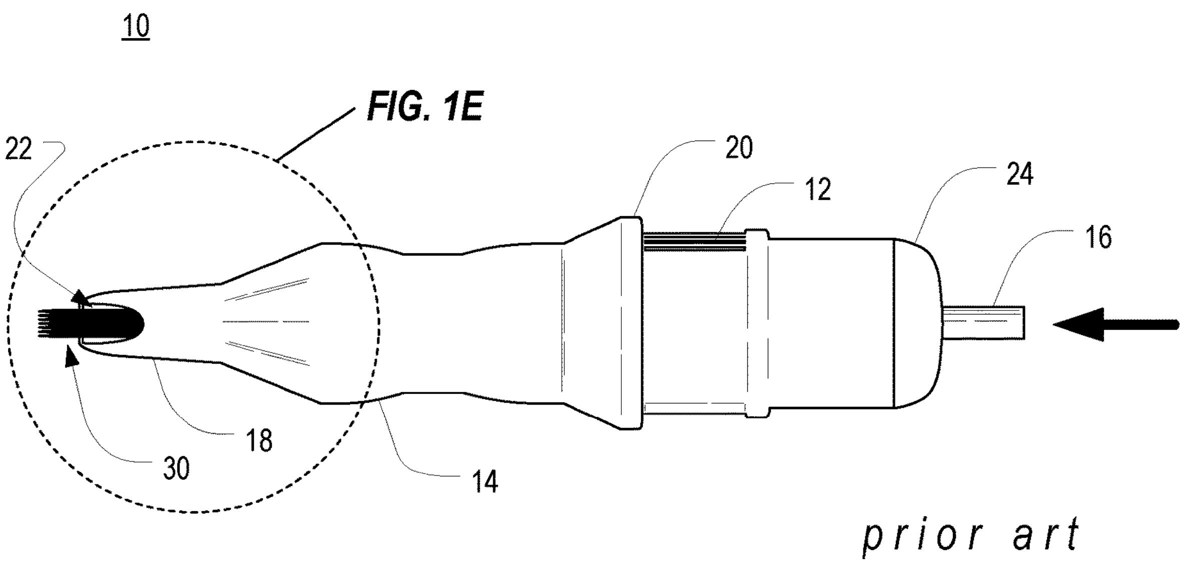
FIG. 1C is a top plan view of the conventional needle cartridge assembly of FIG. 1A, shown with the needle protruding from a tip of a housing.
Figure 1D:
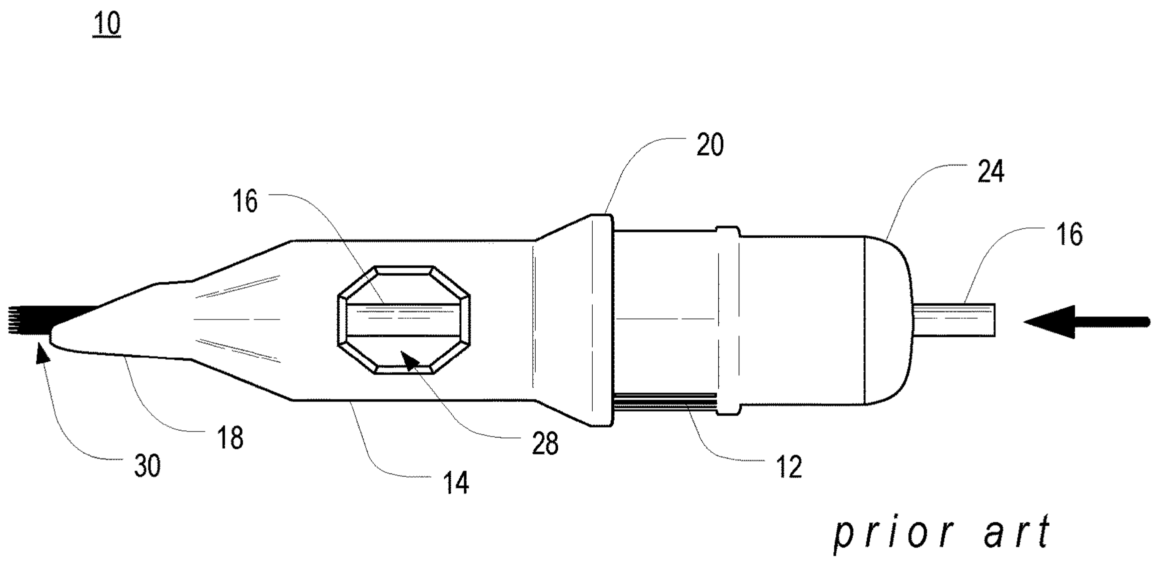
FIG. 1D is a side plan view of the conventional needle cartridge assembly of FIG. 1C.
Figure 1E:
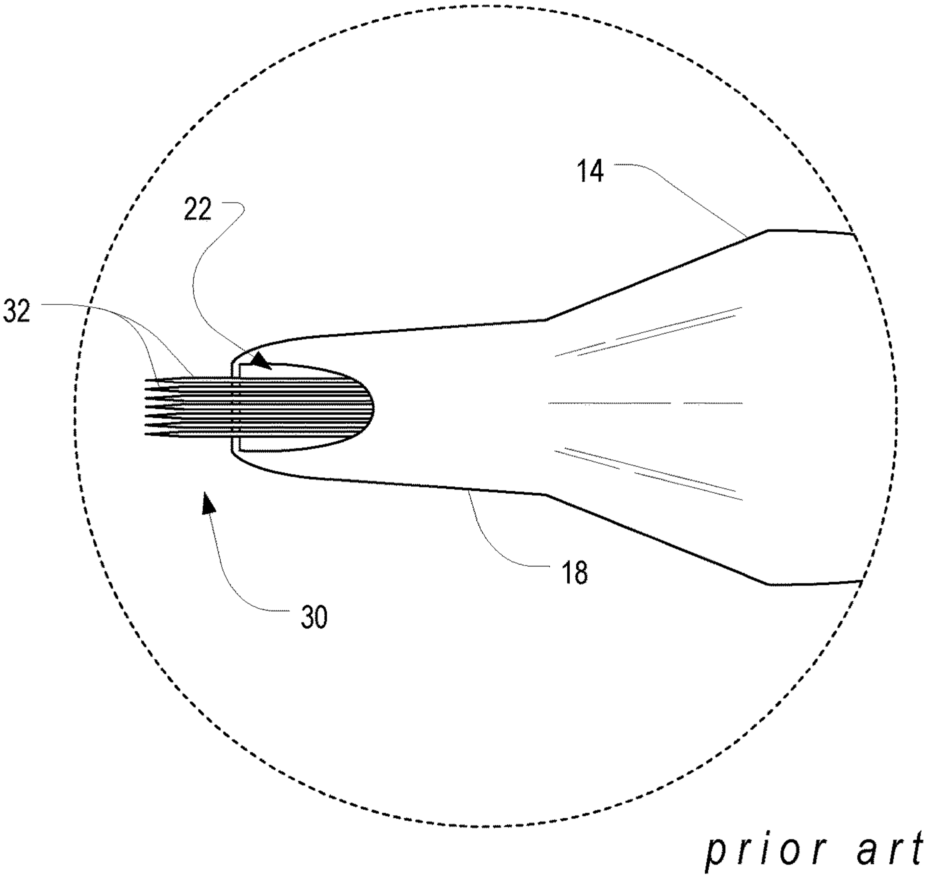
FIG. 1E is a close-up top plan view of the conventional needle cartridge assembly of FIG. 1C, illustrating an arrangement of individual pins of the needle.
Figure 1F:
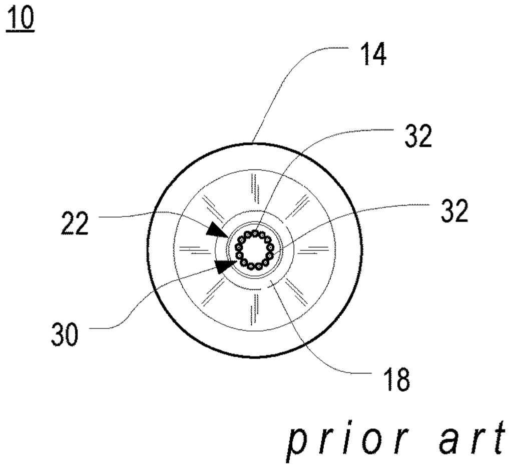
FIG. 1F is a front end plan view of the conventional needle cartridge assembly of FIG. 1C.
Figure 1G:
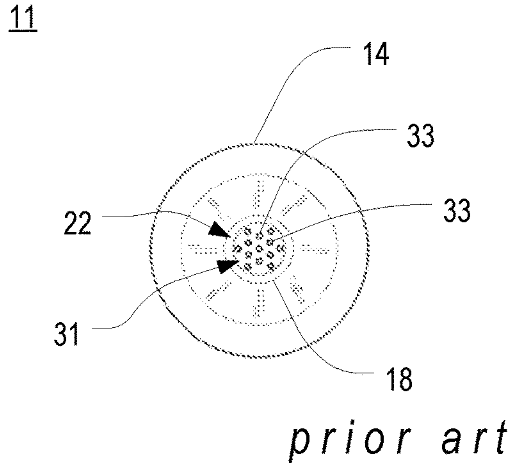
FIG. 1G is a front end plan view of another conventional needle cartridge assembly shown with a needle protruding from a tip of a housing and having an alternative arrangement of individual pins of the needle.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Furthermore, an embodiment of the invention may incorporate only one or a plurality of the aspects of the invention disclosed herein; only one or a plurality of the features disclosed herein; or combination thereof. Moreover, many embodiments, including adaptations, variations, modifications, and equivalent arrangements, are implicitly disclosed herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term-differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112 (f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Further, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

Figure 2A:
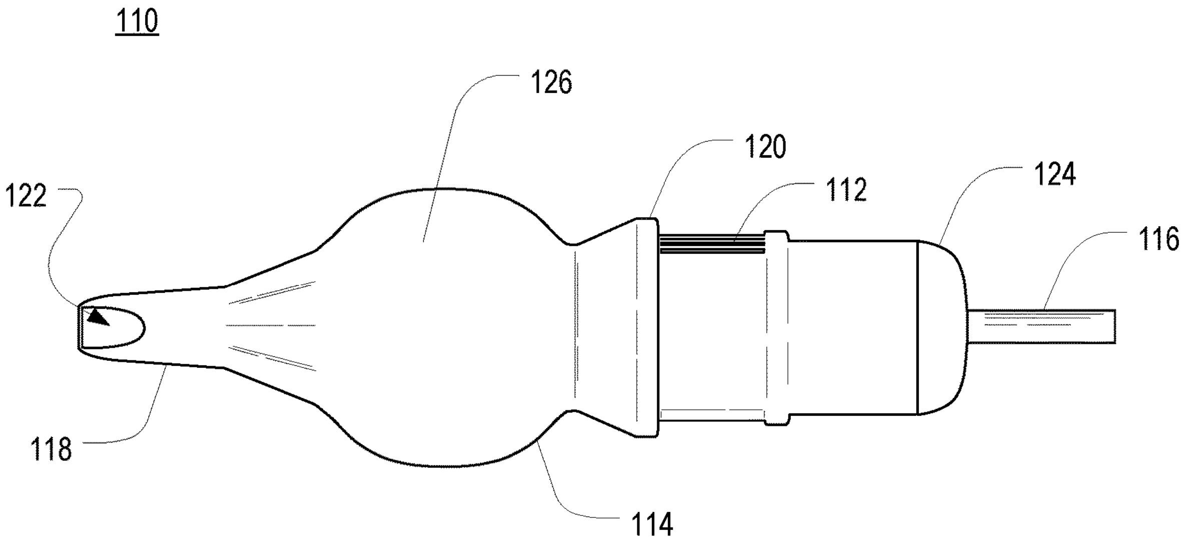
FIG. 2A is a top plan view of a needle cartridge assembly, for use in tattoo removal and/or scar reduction via a tattoo pen, in accordance with one or more aspects of the present invention.
Figure 2B:
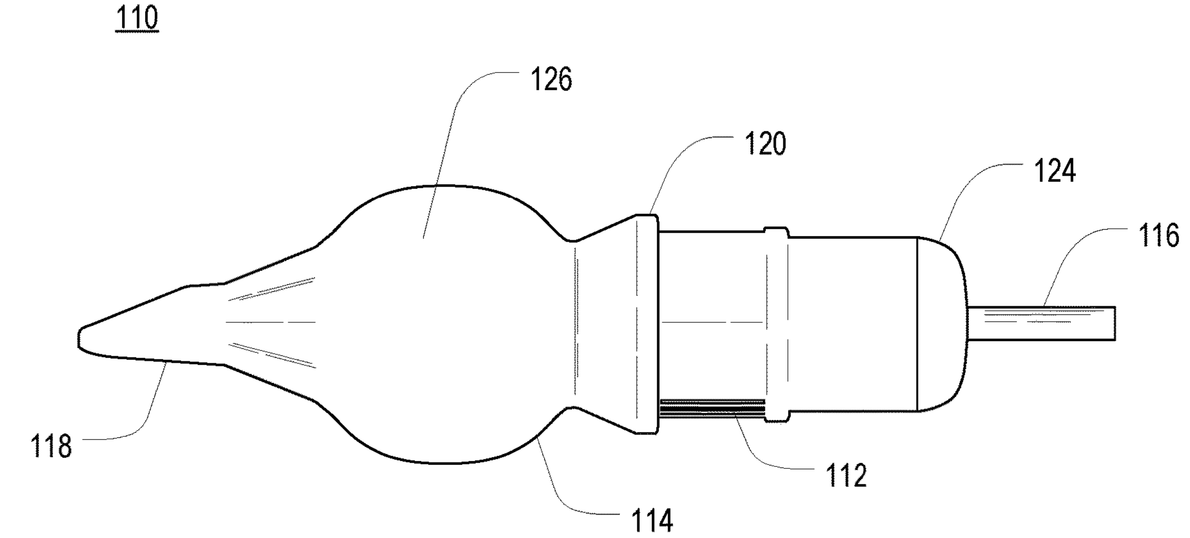
FIG. 2B is a side plan view of the needle cartridge assembly of FIG. 2A.

FIG. 2A is a top plan view of a needle cartridge assembly 110, for use in tattoo removal and/or scar reduction via a tattoo pen 150, in accordance with one or more aspects of the present invention, and FIG. 2B is a side plan view of the needle cartridge assembly 110 of FIG. 2A. In at least some contemplated embodiments, the needle cartridge assembly 110 includes a housing 114 and a tattoo needle (not visible in FIGS. 2A and 2B) affixed to a plunger 116. The housing 114 is securable to a tattoo pen 150 (shown in FIGS. 3A and 3B) and may include surface features 112 to facilitate such securement. As shown in FIGS. 2A and 2B, a rear portion of the housing 114 is designed to be seated within the pen 150 such that a ledge 120 of the housing 114 rests against a distal end of the pen 150. A front portion of the housing 114 is tapered toward a tip 118, which includes an opening 122 through which the needle can pass.

As further shown in FIGS. 2A and 2B, a midsection of the housing 114 includes a bulbous portion 126 that, at its widest, has a diameter or width exceeding that of any other portion or section of the housing 114. The bulbous portion 126 is adjacent to the tip 118, thereby enabling it to be used as a reservoir for retaining liquid removal solution that is drawn into the housing, as will be explained in more detail below. In at least some embodiments, neither the bulbous portion 126 nor any other portion or section of the housing 114 includes side openings, or washouts, to allow excess ink to drain. Absence of washouts in the housing 114, coupled with an enlarged storage capacity owing to the bulbous portion 126, enables the housing to retain a much greater volume of liquid removal solution than a conventional needle cartridge assembly. In at least some embodiments, the housing 114 is made from a clear or translucent material to facilitate ease of viewing an interior of the housing 114.

Figure 2C:
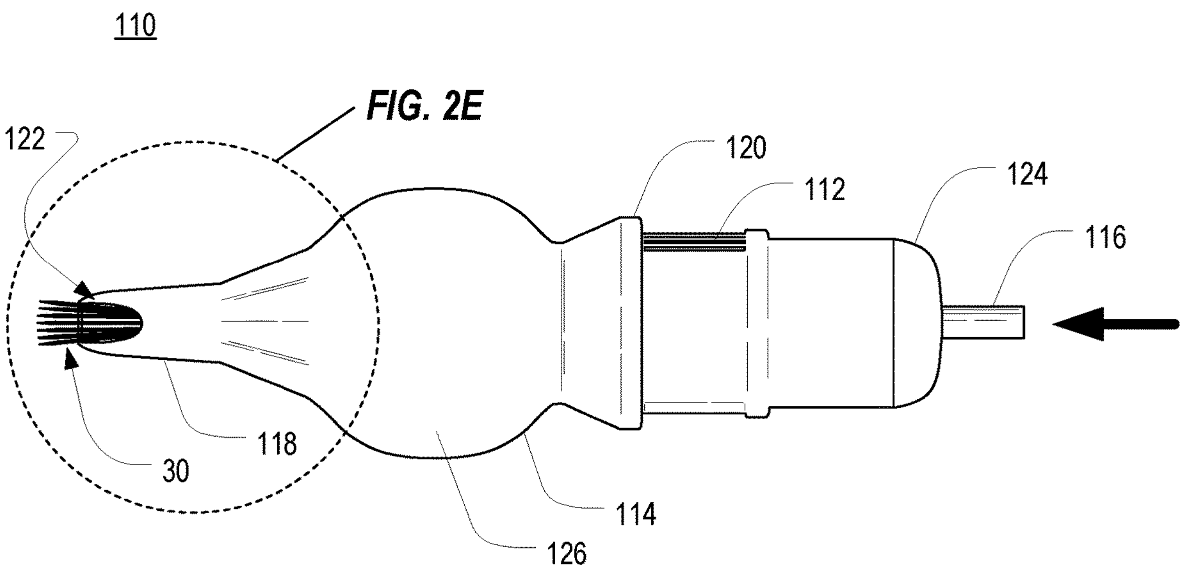
FIG. 2C is a top plan view of the needle cartridge assembly of FIG. 2A, shown with the needle protruding from a tip of a housing.
Figure 2D:
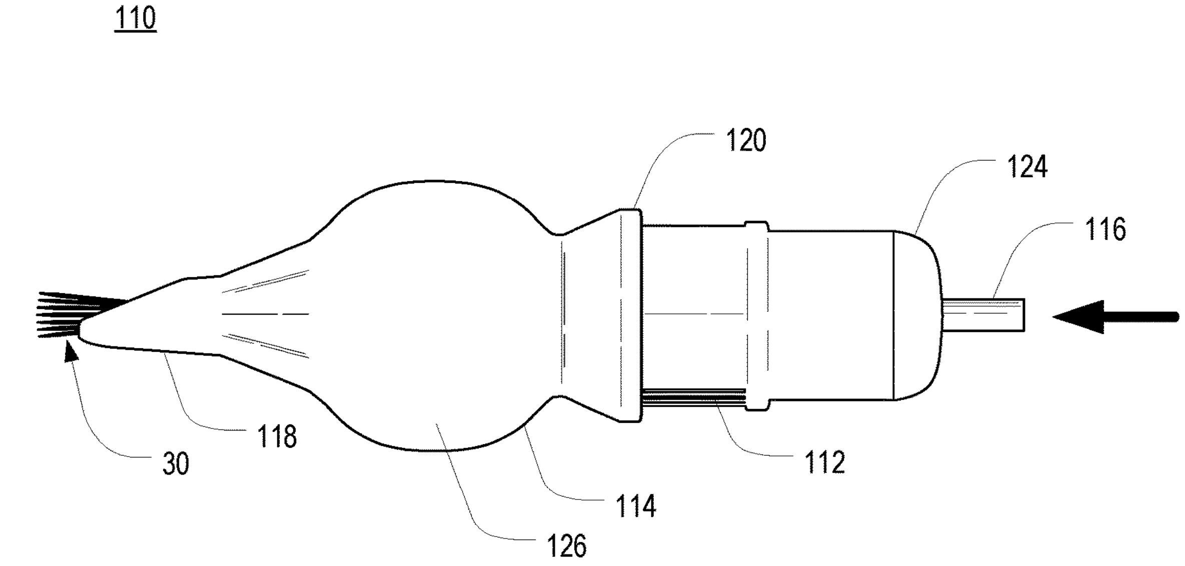
FIG. 2D is a side plan view of the needle cartridge assembly of FIG. 2C.

FIG. 2C is a top plan view of the needle cartridge assembly 110 of FIG. 2A, shown with the needle 130 protruding from a tip 118 of a housing 116, FIG. 2D is a side plan view of the needle cartridge assembly 110 of FIG. 2C. The plunger 116 is shown as a cylindrical rod that extends along the interior cavity of the housing 114 and through an endcap 124 seated at a rear of the housing 114. At a forward end, the plunger 116 includes a tattoo needle 130 that is arranged within the cylindrical profile of the plunger 116. As shown in FIGS. 2C and 2D, the plunger 116 is displaceable along its longitudinal axis by a force, designated by an arrow in FIGS. 2C and 2D, which acts upon the rear end thereof. When applied, the force shifts the plunger 116 forward, against a bias, by a distance that is sufficient for the needle 130 to protrude from the opening 122 at the tip 118 of the housing 114. When the force is withdrawn, the plunger 116 is biased to return to a resting state, with the needle 130 retracting into the internal cavity of the housing 114.

Figure 2E:
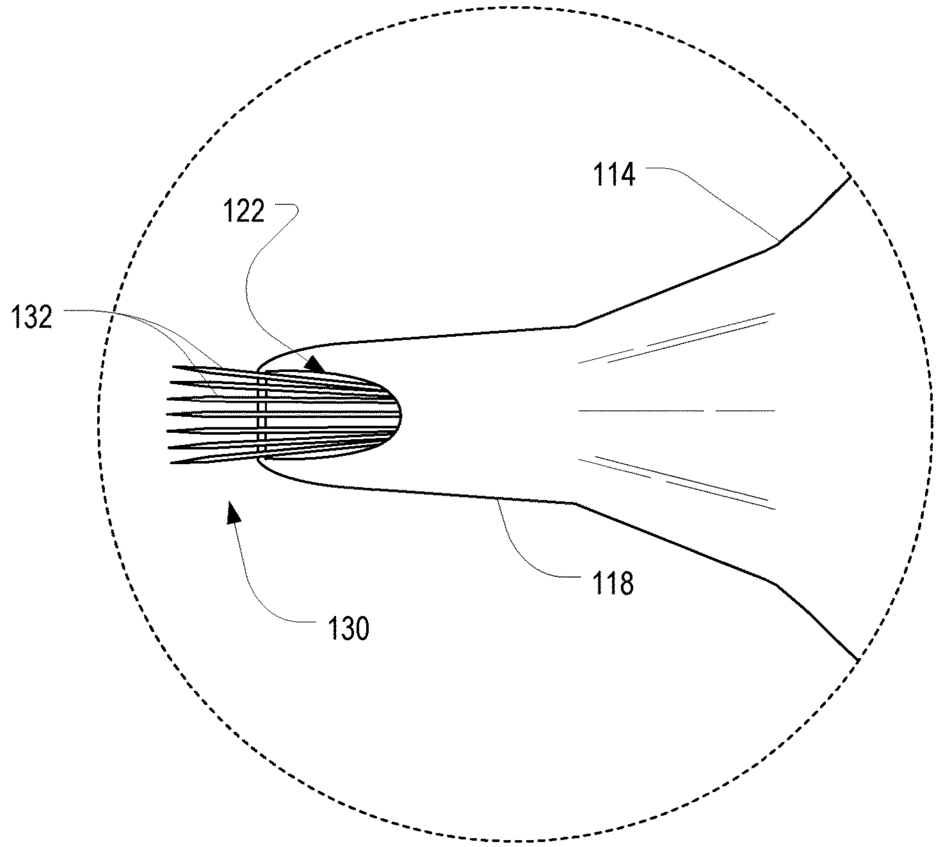
FIG. 2E is a close-up top plan view of the needle cartridge assembly of FIG. 2C, illustrating an arrangement of individual pins of the needle.
Figure 2F:
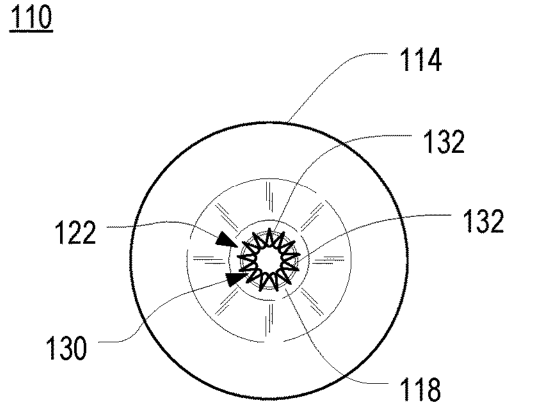
FIG. 2F is a front end plan view of the needle cartridge assembly of FIG. 2C.

FIG. 2E is a close-up top plan view of the needle cartridge assembly 110 of FIG. 2C, illustrating an arrangement of individual pins 132 of the needle 130, and FIG. 2F is a front end plan view of the needle cartridge assembly 110 of FIG. 2C. The needle 130 includes a plurality of solid pins 132 each of which includes a tapered distal end that arrives at a point sharp enough to pierce skin. The arrangement, or grouping, of pins 132 can vary from needle to needle. As shown in FIG. 2F, the illustrated needle 130 includes thirteen individual pins 132 in a 13 round shader arrangement.

Figure 2G:
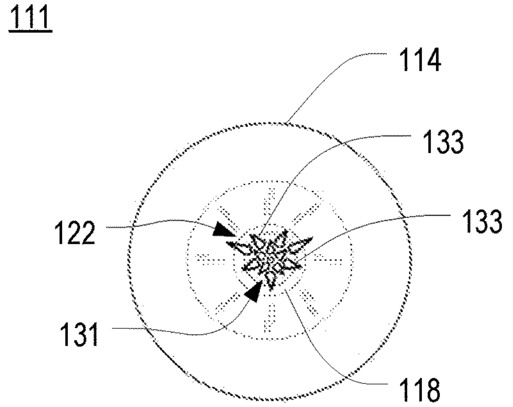
FIG. 2G is a front end plan view of another needle cartridge assembly, for use in tattoo removal and/or scar reduction via a tattoo pen, in accordance with one or more aspects of the present invention, shown with a needle protruding from a tip of a housing and having an alternative arrangement of individual pins of the needle.

Other pin arrangements and pin quantities are likewise contemplated. With respect to the former, it is contemplated that the round shader arrangement may be configured as a hollow or ring-shaped circle of pins (as in FIGS. 2E and 2F) or as a cluster of pins. In this latter regard, FIG. 2G is a front end plan view of another needle cartridge assembly 111, for use in tattoo removal and/or scar reduction via a tattoo pen, in accordance with one or more aspects of the present invention, shown with a needle 131 protruding from a tip 118 of a housing 114 and having an alternative arrangement of individual pins 133 of the needle 131. In FIG. 2G, the needle cartridge assembly 111 is identical to the needle cartridge assembly 110 of FIGS. 2A-2F other than the arrangement of the thirteen pins 133 of the needle 131 in a cluster arrangement. Here, the pins 133 may still be characterized as having an overall generally circular or star-shaped arrangement, but without a ring-like appearance (i.e., the circle or star shape includes pins situated interiorly of the shape). Additionally, in contemplated round shader arrangements that may be implemented in a needle cartridge assembly in accordance with one or more aspects of the present invention, the needle may include nine, eleven, thirteen, fourteen, fifteen, or eighteen individual pins. Each of these contemplated round shader arrangements may be configured either as a circle of pins (as in FIGS. 2E and 2F) or as a cluster of pins (as in FIG. 2G).

With further reference to FIGS. 2C-2G, the pins 132,133 of the needle 130,131 are adapted to fan or flare outward when the needle 130,131 protrudes from the opening 122 at the tip 118 of the housing 114. This action imparts the arrangement of pins 132,133 with a broom-like shape when the plunger 116 is shifted sufficiently forward for the needle 130,131 to protrude from the tip 118. As shown in FIGS. 2C-2G, it is contemplated that the pins 132,133 may flare outward to a such an extent that at least the distal ends of the pins 132,133 extend beyond the cylindrical profile of the plunger 116. It is further contemplated that the pins 132,133 may flare outward to a such an extent that at least the distal ends of the pins 132,133 extend beyond a perimeter of the opening 122.

It is contemplated that the pins 132,133 of the needle 130,131 may fan or flare outward gradually as the plunger 116 is shifted forward. In this regard, the pins 132,133 remain within the cylindrical profile of the plunger 116 when the needle is retracted into the housing. Then, as the plunger 116 is shifted forward, distal ends of the pins 116 gradually fan or flare outwardly away from one another as the needle 130,131 passes through the opening 122. It is further contemplated that the pin arrangement may continue to fan or flare outward all the way up until the needle 130,131 begins to retract, at which point the pins 132,133 begin to retract toward one another to return to a position that is within the cylindrical profile of the plunger 116. When the needle 130,131 is retracted into the housing 114, it is contemplated that individual pins 132,133 of the needle 130,131 may be spaced apart from one another by about 0.25 mm. When the needle 130,131 protrudes from the housing 114 (and when the pin arrangement has reached a maximum point of expansion), it is contemplated that individual pins 132,133 of the needle 130,131 may be spaced apart from one another by as much as about 0.7 mm to about 1 mm.

It is contemplated that a wide variety of different mechanisms may be implemented in connection with the needle cartridge assembly 110,111 to cause the pins 132,133 to fan or flare outward as the needle 130,131 passes through the opening 122. In at least some embodiments, the pins 132, 133 are made from a stainless-steel material. Use of a stainless-steel material imparts the pins 132,133 with malleability that permits the pin arrangement to exhibit an inherent bias causing the pin arrangement to expand when the needle 130,131 is pushed through the opening 122 of the housing 114 and to contract when the needle 130,131 is retracted into the housing 114.

It is contemplated that the pins 132,133 of the needle cartridge assembly 110,111 can be made from a variety of different materials. In at least some contemplated embodiments, the pins 132,133 are made from a carbon steel material. In such cases, the carbon steel material may include a textured or porous surface along at least a portion of the length of each pin. The textured or porous surface adds to the surface area that might otherwise be available to draw a liquid into the needle, thereby allowing each pin to retain a greater quantity of liquid removal solution. In other contemplated embodiments, the pins 132,133 are made from a stainless-steel material. Where a stainless-steel material is used, the pins 132,133 may exhibit greater resistance to corrosion and may be malleable to achieve a modified arrangement (such as the broom arrangement discussed hereinabove).

It is contemplated that dimensions of various features of a needle cartridge assembly 110,111 in accordance with one or more aspects of the present invention may vary. In at least some contemplated embodiments, the bulbous portion 126 of the housing has a maximum width measuring about 1.75 cm. In at least some contemplated embodiments, the tip 118 of the housing 114, where the opening 122 is arranged, may have a width measuring about 5.25 mm. In at least some contemplated embodiments, the housing 114 may have a length measuring about 3.1 cm, each individual pin 132,133 may have a diameter measuring about 0.25 mm, and/or the plunger 116 may have a diameter measuring about 0.35 cm.

Figure 3A:
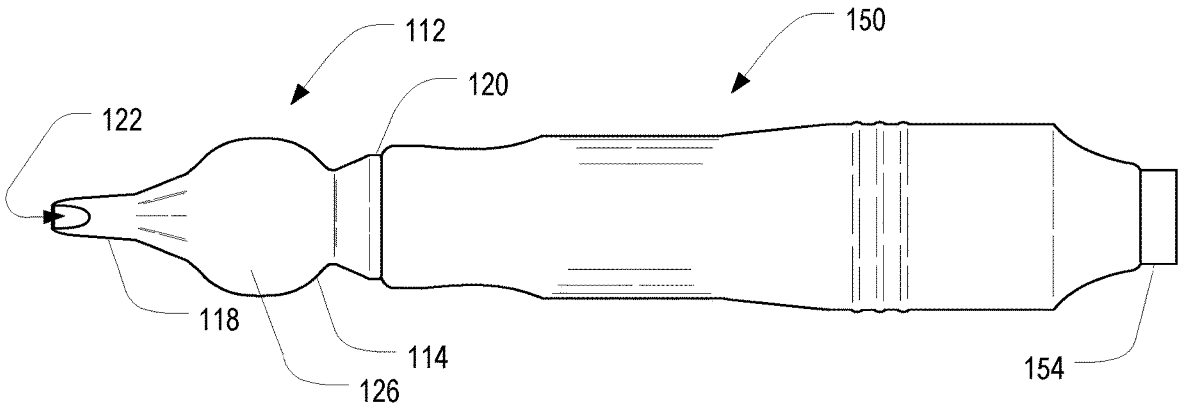
FIG. 3A is a top plan view of the needle cartridge assembly of FIG. 2A, shown installed onto a tattoo pen.
Figure 3B:
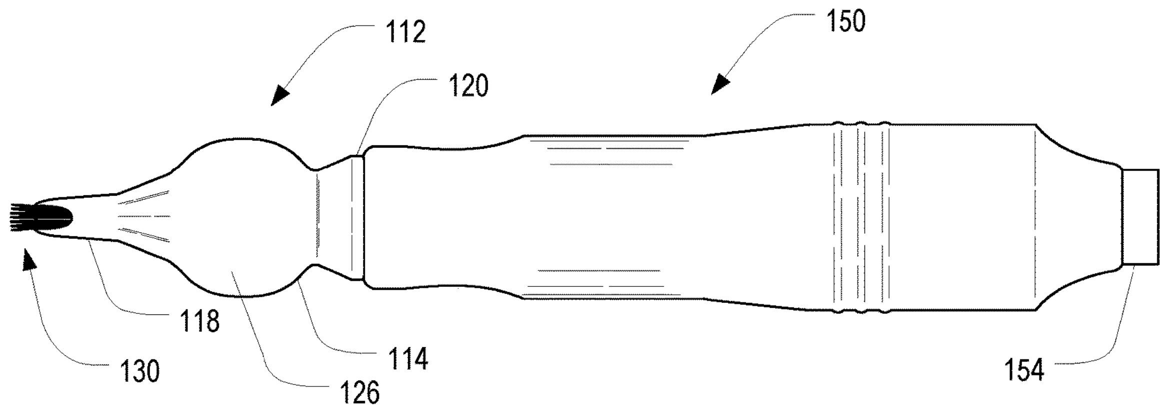
FIG. 3B is a top plan view of the tattoo pen and needle cartridge assembly of FIG. 3A, shown with the needle protruding from the tip of the housing.

FIG. 3A is a top plan view of the needle cartridge assembly 110 of FIG. 2A, shown installed onto a tattoo pen 150, and FIG. 3B is a top plan view of the tattoo pen 150 and needle cartridge assembly 110 of FIG. 3A, shown with the needle 130 protruding from the tip 118 of the housing 114. The conventional needle cartridge assembly 110 of FIGS. 2A-2G is adapted for use with a tattoo pen 150 to pierce the skin and introduce the liquid removal solution in connection with a tattoo removal and/or scar reduction process. Although the tattoo pen 150 of FIGS. 3A and 3B is shown with the needle cartridge assembly 110 of FIGS. 2A-2F installed thereon, it should be appreciated that the needle cartridge assembly 111 of FIG. 2G may be installed and used in connection with the tattoo pen in a tattoo removal and/or scar reduction process in accordance with the methodology set forth hereinbelow in the same or nearly the same manner.

When the needle cartridge assembly 110 is seated onto the tattoo pen 150, the rear end of the plunger 116 is positioned against an actuatable structure of the pen. The tattoo pen 150, which is commonly powered via a DC power source at a rear endcap 154, can be used to actuate the structure to apply a temporary force to the rear end of the plunger 116, thereby deploying the needle 130 as the force is applied and then allowing the needle 130 to retract as the force is removed. In operation, the tattoo pen 150 actuates the structure at rapid intervals to facilitate deployment and retraction of the needle 130 with each actuation (i.e., during an "active" state). The pace of needle deployment and retraction during the active state is commonly at a level that is sufficient to cause the pen 150 to vibrate.

In connection with a tattoo removal process, the pen 150 is dipped into a liquid removal solution to draw solution into the needle 130. It is contemplated that the needle 130 may be deployed through the opening 122 or the pen 130 may be in the active state when dipped into the solution. In contemplated embodiments, the pins 132 extend from the housing 114 by a distance of about 1.5 mm when the needle 130 is fully deployed. Because the pins 132 flare outwardly away from one another as the needle 130 is deployed and retract inwardly toward one another as the needle 130 is retracted, the movement of the pins 132 may resemble a grabbing motion. In this regard, it is contemplated that a grabbing motion can effectively and rapidly collect the liquid removal solution for use in removing a tattoo. As the solution is collected, it is contemplated that solution can be stored within the bulbous portion 126, which, in this regard, functions as a reservoir for collected solution to be used in connection with the tattoo removal process. The absence of washouts in the housing 114 prevents collected solution from seeping out or otherwise draining from the housing 114.

Once the solution has been collected, the pen 150 and needle cartridge assembly 110 are ready for use in removing a tattoo. The pen 150 is positioned near an area of skin having a tattoo to be removed. With the pen 150 in the active state, the needle 130 is deployed in a manner for the pins 132 to create abrasions in the skin. It is contemplated that the needle may be maneuvered in a pattern that resembles small circles to create abrasions in the skin. Unlike with a tattooing process, tattoo removal is less concerned with precise placement of the solution onto the skin. In a tattoo removal process, it is often helpful to be able to deposit a quantity of removal solution to not only the skin that has pigment to be removed, but also the surrounding skin. In this regard, it is contemplated that the bulbous portion 126 of the housing 114 enables the needle cartridge assembly 110 to retain an appropriate volume of removal solution to treat the skin.

In at least some contemplated embodiments, each individual pin 132 has a diameter of about 0.25 mm. With a smaller diameter, individual pins 132 do not require as much pressure to pierce the skin as pins of a larger diameter. It is contemplated that the broom-like arrangement of the pins 132, when the needle 130 is fully deployed, may help to facilitate the solution reaching the correct layer of skin for the tattoo pigment to be removed therefrom. In this regard, it is contemplated in at least some embodiments that the pins 132 extend from the housing 114 by a distance of about 1.5 mm.

It is also contemplated that the small size and broom-like arrangement of the pins 132 upon needle deployment encourages the pins 132 to pierce the skin at a preferred depth for depositing the solution. In this regard, pressure is distributed evenly across the individual pins 132 as the pins engage the surface of the skin. With pressure applied evenly across the pins 132 (as opposed to unevenly, whereby one or more pins bear greater pressure than others), the pins 132 may pierce the skin to nearly the same depth for depositing the removal solution. Advantageously, with evenly distributed pressure across the pins 132, there is less risk of any one of the pins penetrating the skin too deeply, thereby helping to avoid unnecessary injury or loss of removal effectiveness in the treatment process. It is contemplated that even distribution of pressure across the pins can be accomplished with various arrangements of the pins, including the arrangements set forth in each of FIGS. 2F and 2G.

In contemplated embodiments, the liquid removal solution is deposited onto the skin and is absorbed by the skin at locations pierced by the pins 132. In this regard, a pool of removal solution may be formed on the surface of the skin in the area to be treated. Depositing the solution in an effective manner for treatment may be aided by the pin arrangement as well as by flaring movement of the pins 132 as the needle 130 protrudes from the housing 114. For example, it is contemplated that when the needle 130 is retracted within the housing 114, the pins 132 are closer together. When close together, the needle 130 can become saturated with removal solution retained within the housing 114 (which may fill the narrow spaces between the pins 132 by gravity). Saturation of the needle 130 with solution is enhanced by the round shader arrangement of the pins 132, whereby solution collects not only between the pins 132, but also within the circular shape of the pin arrangement. It is contemplated that saturation of the needle 131 may be particularly effective with the pins 133 arranged in a cluster-type round shader, as in FIG. 2G, whereby individual pins 133 are not only adjacent to other pins 133 that define the shape of the arrangement, but also to pins 133 situated interiorly of the defined shape. When the needle 130 is deployed and the pins 132 flare outwardly away from one another, the removal solution may be applied to the skin across a wider area (which is at least wider than a diameter of the pin arrangement when the needle 130 had been fully retracted into the housing 114). In this manner, it is contemplated that the removal solution may be applied to an entire area for treatment (including onto skin that has pigment to be removed as well as surrounding areas).

In connection with a scar reduction process, it is contemplated that the pen 150 and needle cartridge assembly 110 can be deployed in the same manner as described above in connection with removal of a tattoo to reduce a scar or a scarred area on the skin. In this regard, it is contemplated that various advantages arising from use of a needle cartridge assembly 110 in accordance with the present invention in removing a tattoo (such as, for example, increased interior capacity for solution, fanning/flaring of the pin arrangement upon needle deployment, and proper pin piercing depth upon needle deployment) may apply equally well to a method of reducing a scar or a scarred area.

A needle cartridge assembly 110 in accordance with one or more aspects of the present invention is configured to help treat and/or mitigate a variety of different skin ailments. In contemplated embodiments, treatment and/or mitigation of various skin ailments can be accomplished by depositing a liquid solution at a treatment layer of the skin, creating trauma at the treatment layer of the skin, and/or breaking down skin tissue at the treatment layer of the skin.

As noted herein, it is contemplated that a wide variety of different skin ailments may be treatment and/or mitigated through use of a needle cartridge assembly 110 in accordance with one or more aspects of the present invention. Contemplated skin ailments for treatment and/or mitigation include, but are not limited to: allergies; autoimmune disease(s); bacterial or viral infection(s); blood vessel abnormalities; bug bites; cancer(s); clogged pores; diabetes; thyroid disease; skin irritation; structural skin damage; and UV skin damage. It is further contemplated that a needle cartridge assembly 110 in accordance with one or more aspects of the present invention may be used to treat and/or mitigate skin ailments of an unknown cause or stemming from a multitude of causes. Further still, it is contemplated that a needle cartridge assembly 110 in accordance with one or more aspects of the present invention may be used to treat and/or mitigate an unwanted skin function.

With respect to allergy ailments, it is contemplated that a needle cartridge assembly 110 in accordance with one or more aspects of the present invention may be used to treat and/or mitigate skin ailments that include, but are not limited to: allergic contact dermatitis; nickel allergy; poison ivy allergic reaction; poison oak allergic reaction; and poison sumac allergic reaction.

With respect to autoimmune disease ailments, it is contemplated that a needle cartridge assembly 110 in accordance with one or more aspects of the present invention may be used to treat and/or mitigate skin ailments that include, but are not limited to: lupus; alopecia areata; bullous pemphigoid; central centrifugal cicatricial alopecia; epidermolysis bullosa; pemphigus; psoriasis; psoriatic arthritis; scalp psoriasis; and vitiligo.

With respect to bacterial or viral infection ailments, it is contemplated that a needle cartridge assembly 110 in accordance with one or more aspects of the present invention may be used to treat and/or mitigate skin ailments that include, but are not limited to: acne; acne keloidalis nuchae; boils (styes); cellulitis; chickenpox rash; cold sores; folliculitis; genital herpes; genital warts; hand-foot-and-mouth disease; herpes simplex; impetigo; irritant contact dermatitis; leprosy; molluscum contagiosum; monkeypox rash; shingles; syphilis; tinea pedis; and warts.

With respect to blood vessel abnormality ailments, it is contemplated that a needle cartridge assembly 110 in accordance with one or more aspects of the present invention may be used to treat and/or mitigate skin ailments that include, but are not limited to: port-wine stain birthmarks; hemangiomas; and salmon patch birthmarks.

With respect to bug bite ailments, it is contemplated that a needle cartridge assembly 110 in accordance with one or more aspects of the present invention may be used to treat and/or mitigate skin ailments that include, but are not limited to: bed bug bites; Lyme disease; and scabies.

With respect to cancers, it is contemplated that a needle cartridge assembly 110 in accordance with one or more aspects of the present invention may be used to treat and/or mitigate skin ailments that include, but are not limited to: basal cell carcinoma; dermatofibrosarcoma protuberans; cutaneous T-cell lymphoma; melanoma; Merkel cell carcinoma; sebaceous carcinoma; and squamous cell carcinoma.

With respect to clogged pore ailments, it is contemplated that a needle cartridge assembly 110 in accordance with one or more aspects of the present invention may be used to treat and/or mitigate skin ailments that include, but are not limited to, keratosis pilaris.

With respect to diabetes, it is contemplated that a needle cartridge assembly 110 in accordance with one or more aspects of the present invention may be used to treat and/or mitigate skin ailments that include, but are not limited to, diabetic dermopathy.

With respect to thyroid disease, it is contemplated that a needle cartridge assembly 110 in accordance with one or more aspects of the present invention may be used to treat and/or mitigate skin ailments that include, but are not limited to, palmoplantar keratoderma.

With respect to skin irritation ailments, it is contemplated that a needle cartridge assembly 110 in accordance with one or more aspects of the present invention may be used to treat and/or mitigate skin ailments that include, but are not limited to: diaper rash; and prurigo nodularis.

With respect to structural skin damage ailments, it is contemplated that a needle cartridge assembly 110 in accordance with one or more aspects of the present invention may be used to treat and/or mitigate skin ailments that include, but are not limited to: adhesions; burn scar contracture; keloid scars; hypertrophic scarring; and atrophic scarring (stretch marks or acne scars).

With respect to UV skin damage ailments, it is contemplated that a needle cartridge assembly 110 in accordance with one or more aspects of the present invention may be used to treat and/or mitigate skin ailments that include, but are not limited to, actinic keratosis.

With respect to ailments of an unknown cause or stemming from a multitude of causes, it is contemplated that a needle cartridge assembly 110 in accordance with one or more aspects of the present invention may be used to treat and/or mitigate skin ailments that include, but are not limited to: acquired hyperpigmentation; dandruff; dry skin; eczema (atopic dermatitis or dyshidrotic eczema); female pattern hair loss; frontal fibrosing alopecia; granuloma annulare; hair loss; hidradenitis suppurativa; hyperhidrosis; hyperpigmentation; hypopigmentation; ichthyosis; large pores; lichen planus; loose skin; melasma; neurodermatitis; nummular dermatitis; perioral dermatitis; *pityriasis rosea*; rosacea; sarcoidosis; scleroderma; seborrheic dermatitis; seborrheic keratoses; stasis dermatitis; tinea *versicolor*; urticaria; varicose veins; and wrinkles.

With respect to unwanted skin function ailments, it is contemplated that a needle cartridge assembly 110 in accordance with one or more aspects of the present invention may be used to treat and/or mitigate skin ailments that include, but are not limited to: moles; excess hair; and skin tags.

It is contemplated that use of a needle cartridge assembly 110 in accordance with one or more aspects of the present invention in treating and/or mitigating any of the aforementioned skin ailments addresses each ailment in any of a variety of ways, ranging from addressing one or more root causes of the respective ailment to addressing one or more symptoms of the respective ailment.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claim(s) appended hereto and the equivalents thereof.

What is claimed is:

1. A needle cartridge assembly for use with a pen for treatment of skin discoloration or scarring, the needle cartridge assembly comprising:

a housing having an interior cavity, an end with an opening, and a bulbous portion at or near a midsection that is adapted to retain a removal solution; and a needle affixed to a plunger arranged at least partially within the housing, the needle including a plurality of pins extending from an end thereof;

wherein the needle is adapted to be displaceable longitudinally through the interior cavity to maneuver the plurality of pins through the opening; and wherein the plurality of pins is adapted to flare outward at least upon passing through the opening.

2. The needle cartridge assembly of claim 1, wherein the plurality of pins is adapted to flare outward gradually as the needle is displaced.

3. The needle cartridge assembly of claim 1, wherein the plurality of pins has a shape in profile.

4. The needle cartridge assembly of claim 3, wherein the plurality of pins retains the shape as the plurality of pins flares outward.

5. The needle cartridge assembly of claim 4, wherein a perimeter of the shape after needle displacement through the opening is greater than that of the shape prior to needle displacement through the opening.

6. The needle cartridge assembly of claim 1, wherein the plurality of pins includes thirteen pins.

7. The needle cartridge assembly of claim 1, wherein the plurality of pins has a round shader arrangement.

8. The needle cartridge assembly of claim 1, wherein the needle is adapted to be retractable to withdraw the plurality of pins through the opening and into the interior cavity.

9. The needle cartridge assembly of claim 8, wherein the plurality of pins is adapted to retract inward at least upon passing through the opening into the interior cavity.

10. The needle cartridge assembly of claim 9, wherein the plurality of pins is adapted to retract inward gradually as the needle is retracted into the interior cavity.

11. The needle cartridge assembly of claim 1, wherein a widest section of the bulbous portion has a width exceeding that of any other portion of the housing.

12. The needle cartridge assembly of claim 11, wherein the bulbous portion includes one or more curved walls.

13. The needle cartridge assembly of claim 1, wherein each of the plurality of pins is made from a carbon steel material.

14. The needle cartridge assembly of claim 13, wherein one or more of the plurality of pins includes a porous surface along at least a portion of a length thereof.

15. The needle cartridge assembly of claim 1, wherein each of the plurality of pins is made from a stainless-steel material.

16. A method of treating skin discoloration or scarring comprising:

attaching a needle cartridge assembly to a pen, the needle cartridge assembly including a housing, having an interior cavity and an end with an opening, and a needle affixed to a plunger that is arranged at least partially within the housing, wherein the needle includes a plurality of pins extending from an end thereof, and is longitudinally displaceable through the interior cavity to maneuver the plurality of pins through the opening;

loading the plurality of pins with a removal solution contained at a bulbous portion at or near a midsection of the housing;

actuating the needle, via a force applied by the pen against the plunger, to deploy the plurality of pins through the opening, whereupon the plurality of pins flares outward at least upon passing through the opening; and piercing skin of a treatment area via the plurality of pins, thereby depositing at least some of the loaded removal solution at a layer for treatment of skin discoloration or scarring.

17. The method of claim 16, wherein a piercing pressure is distributed evenly across the pins.

18. The method of claim 16, wherein the plurality of pins has a shape in profile that is retained as the plurality of pins flares outward.

19. The method of claim 16, wherein the plurality of pins flares outward gradually as the needle is actuated.

20. The method of claim 16, wherein the plurality of pins has a round shader arrangement.

* * * * *